(12) United States Patent
Yoshiuchi et al.

(10) Patent No.: US 8,297,351 B2
(45) Date of Patent: Oct. 30, 2012

(54) DOWNHOLE SENSING SYSTEM USING CARBON NANOTUBE FET

(75) Inventors: Hidetoshi Yoshiuchi, Fujisawa (JP); Tsutomu Yamate, Yokohama (JP); John Ullo, Sudbury, MA (US); Kazuhiko Matsumoto, Suita (JP)

(73) Assignee: Schlumberger Technology Corporation, Sugar Land, TX (US)

( * ) Notice: Subject to any disclaimer, the term of this patent is extended or adjusted under 35 U.S.C. 154(b) by 993 days.

(21) Appl. No.: 12/332,304

(22) Filed: Dec. 10, 2008

(65) Prior Publication Data

US 2012/0118558 A1 May 17, 2012

Related U.S. Application Data

(60) Provisional application No. 61/016,820, filed on Dec. 27, 2007.

(51) Int. Cl.
*E21B 47/00* (2012.01)
(52) U.S. Cl. ............................... 166/250.01; 73/152.51
(58) Field of Classification Search .......... 166/250.01, 166/66; 73/152.51; 257/24, 414
See application file for complete search history.

(56) References Cited

U.S. PATENT DOCUMENTS

| 3,780,575 | A | 12/1973 | Urbanosky |
| 3,859,851 | A | 1/1975 | Urbanosky |
| 4,765,184 | A | 8/1988 | Delatorre |
| 4,860,581 | A | 8/1989 | Zimmerman et al. |
| 6,630,890 | B1 | 10/2003 | Endo et al. |
| 2004/0160726 | A1 | 8/2004 | Lerche et al. |
| 2004/0253741 | A1 | 12/2004 | Star et al. |
| 2005/0178282 | A1 | 8/2005 | Brooks et al. |
| 2007/0006583 | A1 | 1/2007 | Veneruso |
| 2007/0105249 | A1 | 5/2007 | Veneruso et al. |
| 2007/0132043 | A1 | 6/2007 | Bradley et al. |
| 2008/0063566 | A1* | 3/2008 | Matsumoto et al. ......... 422/68.1 |
| 2009/0045061 | A1* | 2/2009 | Farrow et al. ................ 204/471 |
| 2009/0072137 | A1* | 3/2009 | Hunt et al. .................... 250/305 |
| 2010/0032653 | A1* | 2/2010 | Takeda et al. ................... 257/24 |
| 2011/0163296 | A1* | 7/2011 | Pace et al. ....................... 257/24 |
| 2011/0165557 | A1* | 7/2011 | Ah et al. ............................ 435/5 |
| 2011/0183438 | A1* | 7/2011 | Matsumoto et al. .......... 436/501 |

FOREIGN PATENT DOCUMENTS

| WO | 2005/066618 | 7/2005 |
| WO | 2005/084378 | 9/2005 |

OTHER PUBLICATIONS

Misewich J A, et al, "Electrically induced optical emission from a carbon Nanotube FET", Science, American Assoc. for the Advancement of Science, Washington, DC, US, vol. 300, May 2, 2003 pp. 783-786.

* cited by examiner

*Primary Examiner* — Daniel P Stephenson
(74) *Attorney, Agent, or Firm* — Jianguang Du; Jody DeStefanis

(57) ABSTRACT

Subterranean sensing devices configured or designed for downhole use to sense a local condition in the well. The sensing devices comprise one or more transistor having at least one carbon nanotube field effect transistor (CNT FET) configured or designed for operation downhole, within a borehole.

19 Claims, 15 Drawing Sheets

$C_G$ : GATE CAPACITANCE

|  | $C_G$ [F] | $\Delta V_G = e^-/\Delta C_G$ [V] |
|---|---|---|
| Si FET | $10^{-15}$ | 0.0001 |
| CNT FET | $10^{-17} \sim 10^{-18}$ | $0.1 \sim 0.01$ |

F I G . 9
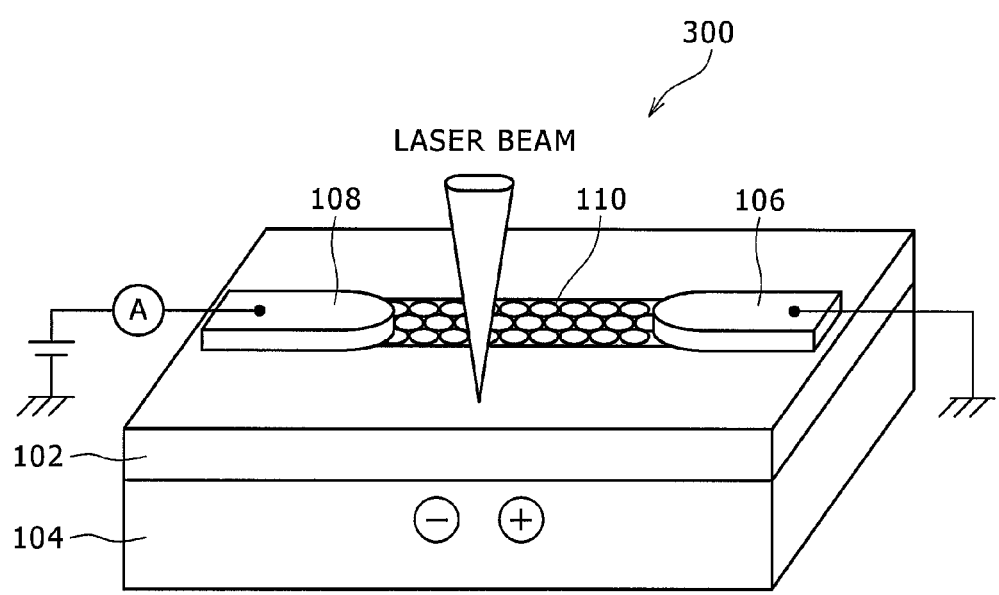

1) PHOTO RESIST PATTERNING

2) Fe DEPOSITION

3) LIFT OFF

4) CARBON NANOTUBE GROWTH

900C/30MIN.

CHEMICAL SENSOR MODULE

MFC IN CHEMICAL SENSOR

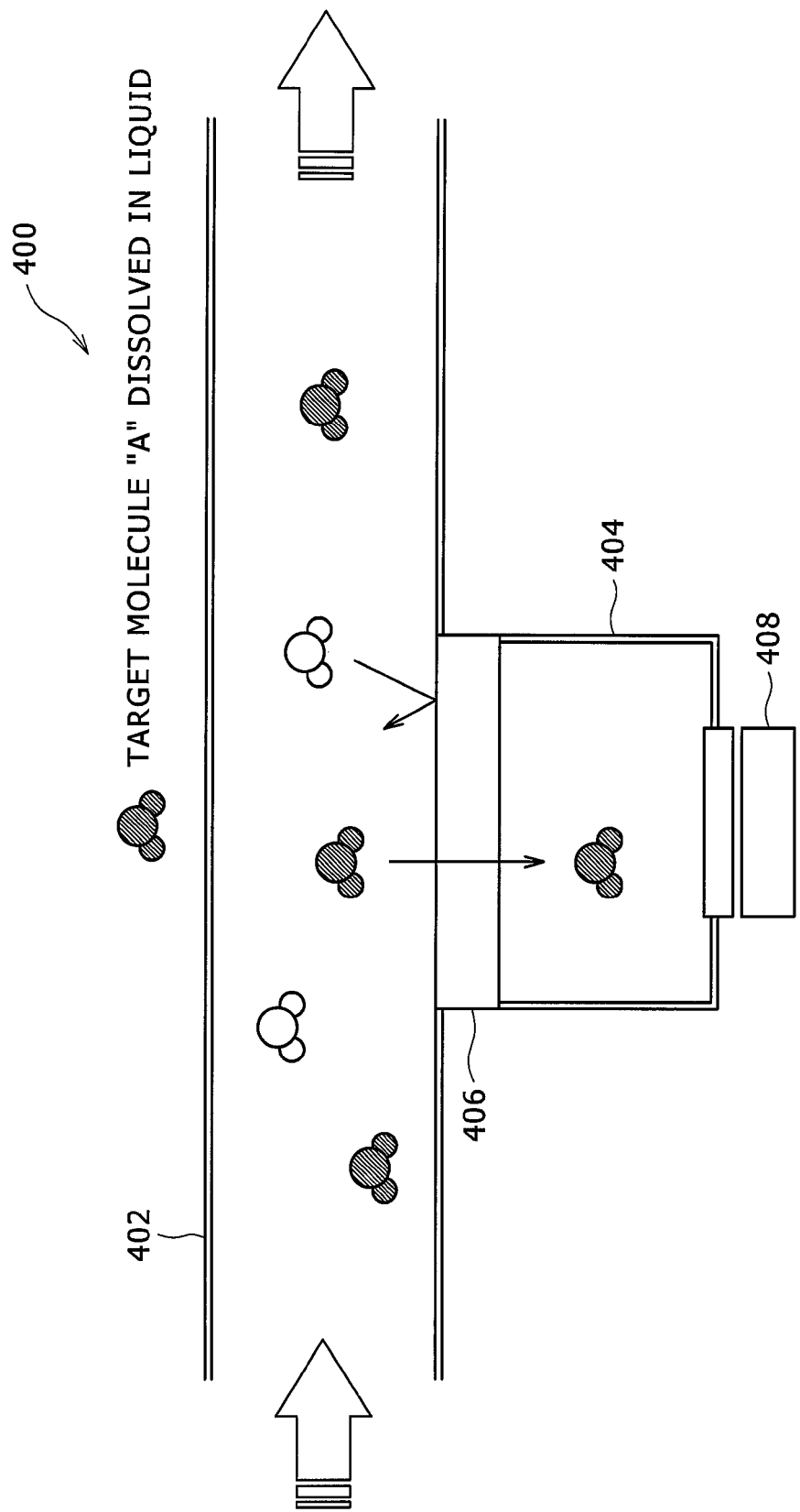

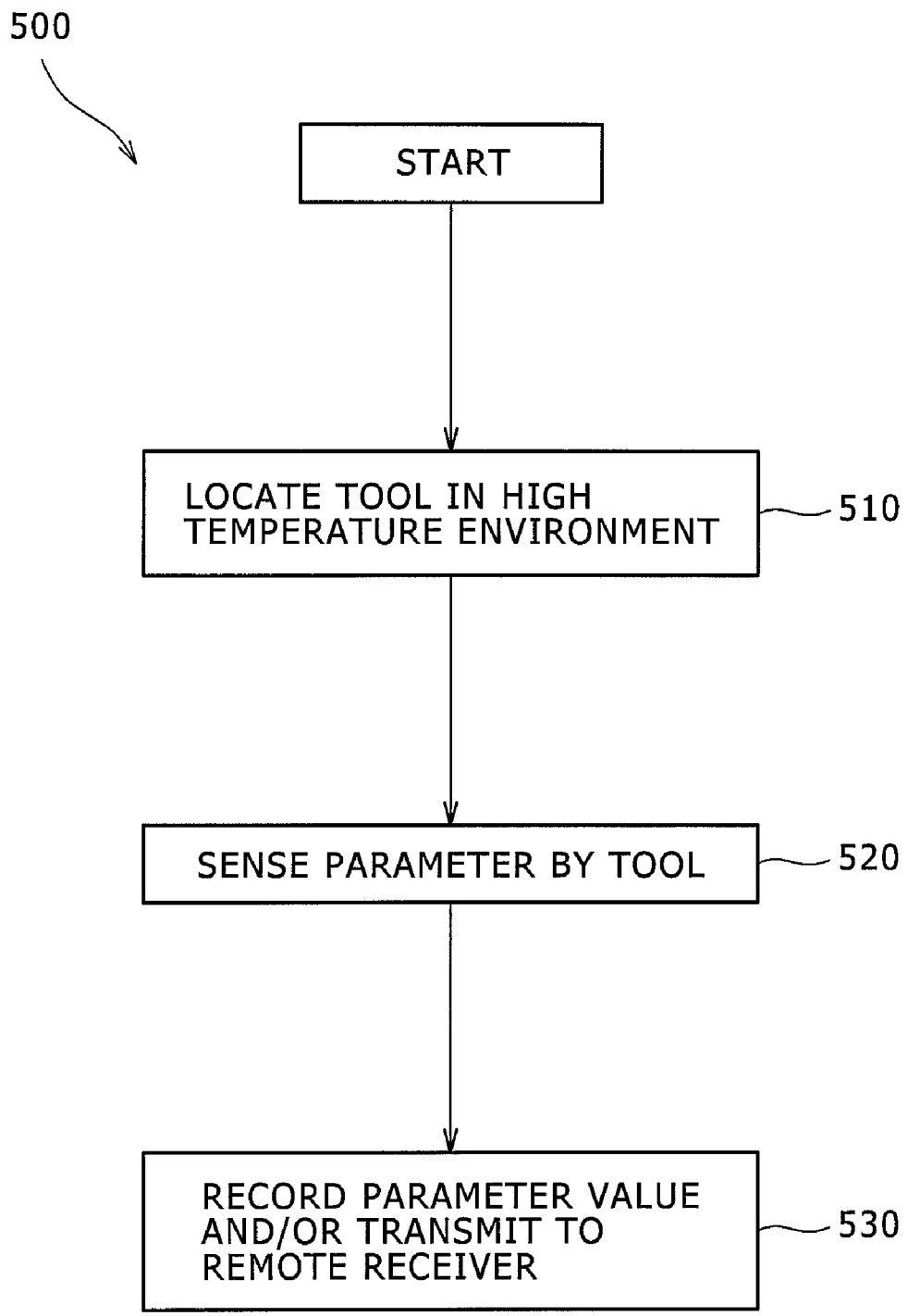

DOWNHOLE SENSING SYSTEM USING CARBON NANOTUBE FET

RELATED APPLICATIONS

This application claims priority of U.S. Provisional Patent Application Ser. No. 60/016,820, filed 27 Dec. 2007, the entire contents of which are incorporated herein by reference.

FIELD

The present disclosure relates generally to downhole systems for gathering data from subterranean formations. More particularly, the present disclosure relates to downhole sensing systems having devices that are configured or designed using carbon nanotube field effect transistors (CNT FET). Such sensing systems may be used for collecting and storing downhole data in high temperature conditions.

BACKGROUND

Logging and monitoring boreholes has been done for many years to enhance and observe recovery of oil and gas deposits. Data relating to earth formations are acquired by logging operations for purposes of exploration, development and management of hydrocarbon or water reservoirs, and sequestration of substances such as $CO_2$. Such operations, including wireline logging, measurement-while-drilling (MWD) and logging-while-drilling (LWD), typically use a downhole tool having various sensing components for collecting, storing, and transmitting data.

In the logging of boreholes, one method of making measurements underground includes attaching one or more tools to a wireline connected to a surface system. The tools are then lowered into a borehole by the wireline and drawn back to the surface ("logged") through the borehole while taking measurements. The wireline is usually an electrical conducting cable with limited data transmission capability.

Similarly, permanent monitoring systems are established with permanent sensors that are also generally attached to an electrical cable. After drilling a well, various sensing components may be fixed to production tubing for purposes of analyzing hydrocarbons and other fluids present in the wellbore, and for control of fluid flows in the wellbore. In this, various sensing components typically are used for purposes of production logging.

Long term reservoir monitoring and permanent monitoring are other applications that require deployment of sensors in completed wells. Sensor arrays may be deployed in a well by various means and sensor data gathered and transmitted uphole by a telemetry system for processing and analysis.

Recent developments in drilling technology require that downhole tools be capable of effectively collecting various data with high sensitivity or selectivity while drilling in oilfield or downhole environments. In this, there is a need for improved sensing systems that are able to acquire various data with high sensitivity or selectivity in a real-time manner.

SUMMARY

The present disclosure addresses the above-described needs and others. Specifically, the present disclosure provides devices for downhole, high-temperature systems and methods that may be particularly useful for subterranean investigation tools.

In consequence of the background discussed above, and other factors that are known in the field of oilfield exploration and development, management of water reservoirs, and sequestration of substances such as $CO_2$, some embodiments of sensing systems are disclosed herein comprising sensor devices that are suitable for effective data acquisition in oilfield or subterranean environments. The sensor devices use one or more carbon nanotube field effect transistors (CNT FETs) to provide higher sensitivity and a smaller sensor for downhole use.

In one aspect of the present disclosure, a subterranean tool is configured to operate downhole in a well traversing a formation. In some aspects, the tool comprises a sensing device configured or designed for downhole use to sense a local condition in the well, wherein the sensing device comprises at least one carbon nanotube field effect transistor (CNT FET) configured or designed for operation downhole, within a borehole. The at least one CNT FET may be configured or designed for sensing physical and/or chemical characteristics downhole, within a borehole.

In certain aspects of the present disclosure, the at least one CNT FET comprises a side-gate FET. In other aspects herein, the one or more CNT FET comprises a top-gate FET. In yet other aspects, the CNT FETs comprise a back-gate FET. In further aspects of the present disclosure, the CNT FETs comprise a co-axial gate FET.

The at least one CNT FET may be configured or designed for use at downhole temperatures in excess of about 115 degrees Celsius, for example, at temperatures of about 200 degrees Celsius. In certain aspects of the present disclosure, the CNT FETs may be modified to function as a chemical probe. In other aspects herein, a chemical probe may be fixed to a CNT FET.

A CNT FET may be configured or designed to function as various optical devices for downhole applications. In some possible embodiments, the sensing device comprises at least one optical device, the optical device comprising the at least one CNT FET configured or designed to function as a photosensitive detector downhole, within a borehole. The subterranean tool may comprise one or more optical communications module including the at least one optical device. The subterranean tool may comprise one or more downhole fluid analysis module including the at least one optical device.

In further embodiments, the sensing device comprises a chemical sensor. The chemical sensor may comprise a gas detector.

A downhole chemical sensing system according to the present disclosure comprises a surface data acquisition unit comprising a surface telemetry unit; a downhole telemetry cartridge; a communications interface between the surface data acquisition unit and the downhole telemetry cartridge; a downhole tool; and a downhole electrical tool bus operatively connected between the downhole telemetry cartridge and the downhole tool, wherein the downhole tool comprises a chemical sensing device configured or designed for downhole use to sense a local condition in a well. The chemical sensing device comprises one or more carbon nanotube field effect transistor (CNT FET) configured or designed for operation downhole, within a borehole, to sense chemical characteristics.

A fluid analysis system according to the present disclosure is configured to operate downhole at elevated temperatures in excess of about 115 degrees Celsius in a well traversing a formation. In certain aspects, the system comprises at least one optical sensor to measure signals of interest and determine properties of formation fluids downhole, within a borehole, wherein the at least one optical sensor comprises one or more carbon nanotube field effect transistor (CNT FET) configured or designed for operation downhole, within a borehole, as a photo-sensitive detector. In further aspects, the CNT FET may be configured or designed for operation downhole, within a borehole, at temperatures in excess of about 115 degrees Celsius.

Additional advantages and novel features will be set forth in the description which follows or may be learned by those skilled in the art through reading these materials or practicing the invention. The advantages of the invention may be achieved through the means recited in the attached claims.

BRIEF DESCRIPTION OF THE DRAWINGS

The accompanying drawings illustrate preferred embodiments of the present invention and are a part of the specification. Together with the following description, the drawings demonstrate and explain principles of the present invention.

FIG. 9 is a schematic view of a light receiving element or photo detector according to the present disclosure;

FIGS. 12(a) and 12(b) show one possible CNT FET chemical sensing system for dissolved chemicals according to the present disclosure; and FIG. 13 is a flowchart of one possible method in accordance with embodiments of the present disclosure.

Figure 1:
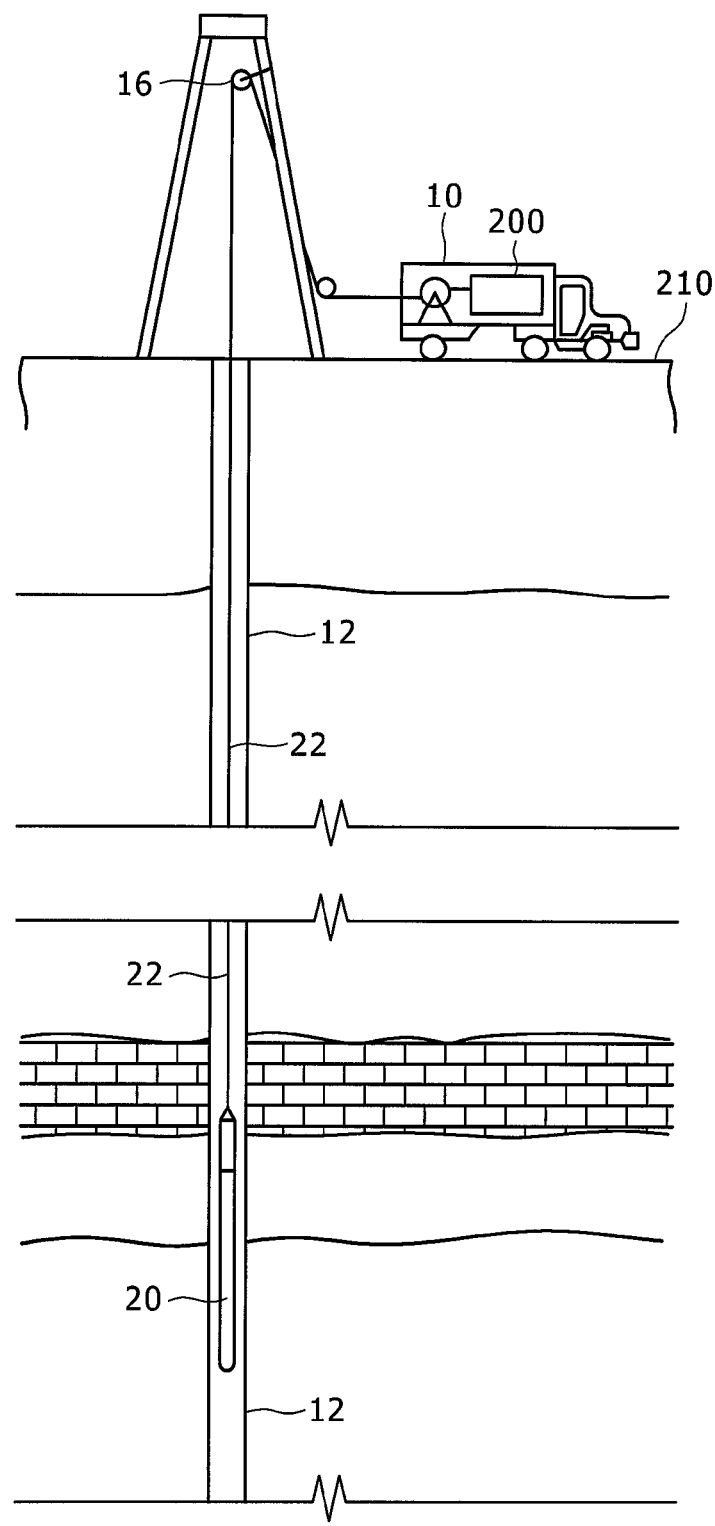
FIG. 1 shows one possible operational context for a downhole tool sensing system in accordance with the disclosure herein.

Throughout the drawings, identical reference numbers indicate similar, but not necessarily identical elements. While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the scope of the invention as defined by the appended claims.

DETAILED DESCRIPTION

Illustrative embodiments and aspects of the invention are described below. In the interest of clarity, not all features of an actual implementation are described in the specification. It will of course be appreciated that in the development of any such actual embodiment, numerous implementation-specific decisions must be made to achieve the developers' specific goals, such as compliance with system-related and business-related constraints that will vary from one implementation to another. Moreover, it will be appreciated that such development effort might be complex and time-consuming, but would nevertheless be a routine undertaking for those of ordinary skill in the art having benefit of the disclosure herein.

Reference throughout the specification to "one embodiment" or "an embodiment" or "some embodiments" means that a particular feature, structure, or characteristic described in connection with the embodiment is included in at least one embodiment of the present disclosure. Thus, the appearance of the phrases "in one embodiment" or "in an embodiment" or "in some embodiments" in various places throughout the specification are not necessarily all referring to the same embodiment. Furthermore, the particular features, structures, or characteristics may be combined in any suitable manner in one or more embodiments.

As used throughout the specification and claims, the term "downhole" refers to a subterranean environment, particularly in a wellbore. "Downhole tool" is used broadly to mean any tool used in a subterranean environment including, but not limited to, a logging tool, an imaging tool, an acoustic tool, a permanent monitoring tool, and a combination tool. "High temperature" refers to downhole temperatures in excess of about 115 degrees Celsius. "Optical device" is used broadly to mean any device that creates, manipulates, or measures electromagnetic radiation, i.e., a device for producing or controlling light. The words "including" and "having" shall have the same meaning as the word "comprising."

Moreover, inventive aspects lie in less than all features of a single disclosed embodiment. Thus, the claims following the Detailed Description are hereby expressly incorporated into this Detailed Description, with each claim standing on its own as a separate embodiment.

The present disclosure contemplates various downhole tools and systems that utilize one or more CNT FETs that are configured or designed for purposes of sensing data relating to environmental and tool parameters downhole, within a borehole. In this, the tools and sensing systems disclosed herein may effectively sense and store characteristics relating to components of downhole tools as well as formation parameters at elevated temperatures and pressures. Chemicals and chemical properties of interest in oilfield exploration and development may also be measured and stored by the sensing systems contemplated by the present disclosure. The sensing systems herein may be incorporated in tool systems such as wireline logging tools, measurement-while-drilling and logging-while-drilling tools, permanent monitoring systems, drill bits, drill collars, sondes, among others. For purposes of this disclosure, when any one of the terms wireline, cable line, slickline or coiled tubing or conveyance is used it is understood that any of the above-referenced deployment means, or any other suitable equivalent means, may be used with the present disclosure without departing from the spirit and scope of the present invention.

The present disclosure provides some embodiments directed towards improving, or at least reducing, the effects of one or more of the above-identified problems and others that are known in the art.

Some CNTs with semiconducting behavior and good electron transport properties are suitable for heat-resistant and high-speed electronics devices. Such CNTs often have a zigzag chiral-type structure. However, other general chiral types exhibiting semiconducting properties may also be used according to the principles of the present disclosure. Particularly, when these CNTs are applied to a transistor such as a field effect transistor (FET), the transistor is capable of effectively sensing physical and/or chemical characteristics with sensitivities comparable to or greater than Si FETs.

In one of many possible embodiments, a high-temperature downhole oilfield sensor system is provided. In other possible embodiments, a high-temperature downhole telemetry system is provided. The high-temperature downhole oilfield systems comprise a downhole optical device, and, optionally, a communication fiber or cable extending between the downhole system and a surface data acquisition system, wherein the downhole optical device comprises one or more transistor configured or designed for high-temperature downhole applications, such as a CNT FET suitable for withstanding high-temperature operations of at least 115 degrees Celsius.

The principles described herein contemplate methods and apparatus facilitating sensing and communication, with chemical sensors, fluid analysis sensors, or otherwise, using downhole tools and sensors in high temperature applications. The use of CNT FETs in downhole tools provides higher sensitivity and selectivity in sensing than previously available. The principles described herein facilitate sensing and communications between downhole tools and sensors, and associated surface systems, even in high temperature environments.

As previously discussed above, demand for higher resolution sensing tools is growing rapidly. The present disclosure provides enabling technology for sensing systems in high-temperature downhole environments. The solutions proposed herein reduce tool and system costs, improve tool reliability, and provide high sensitivity tool sensors. The tool architecture described herein provide significant expansion capability to existing tool architecture allowing greater functionality and services to be provided by existing tools. In this, as a consequence of the ideas in the present disclosure new tool designs and applications are possible that were not realizable with the presently available systems.

In some embodiments, the present disclosure is applicable to oilfield exploration and development in areas such as downhole fluid analysis using one or more fluid analysis modules in, for example, Schlumberger's Modular Formation Dynamics Tester (MDT). The downhole tools disclosed herein have applicability in extreme conditions such as oilfield environments. Such downhole tools may be used for collecting and storing downhole data in high temperature conditions.

FIG. 1 is an exemplary embodiment of a system for downhole analysis and sampling of formation fluids utilizing a downhole tool according to the present disclosure. FIG. 1 depicts one possible setting for utilization of the present invention and other operating environments also are contemplated by the present disclosure.

In FIG. 1, a service vehicle 10 is situated at the formation surface 210 of a wellsite having a borehole or wellbore 12 with a downhole tool 20 suspended in the borehole 12. The downhole tool 20 typically is suspended from the lower end of a cable 22 spooled on a winch or cable drum 16 at the formation surface 210. The downhole tool 20 needs to withstand high temperatures as the borehole 12 may have high temperature conditions such as 115 degrees Celsius or above.

Typically, the borehole 12 contains a combination of fluids such as water, mud filtrate, formation fluids, and the like. The downhole tool 20 may be used for testing earth formations and analyzing the composition of fluids from a formation. The downhole tool 20 may be used to measure various parameters such as, for example, flow rates, temperatures, pressures, fluid properties, gamma radiation properties, and the like. Additionally, the downhole tool 20 may have functions to monitor fluid injection, formation fracturing, seismic mapping, and the like. The downhole tool 20 may be a wireline tool, a wireline logging tool, a downhole tool string, or other known means of deployment such as a drill collar, a sonde, a drill bit, a measurement-while-drilling tool, a logging-while-drilling tool, a permanent monitoring tool, and the like.

Sensing devices disclosed herein include micro electromechanical systems (MEMS). The present disclosure contemplates that the downhole tool 20 using high temperature electronics may be used for purposes of sensing, storing, and transmitting data relating to environmental and tool parameters. In this, the devices disclosed may effectively sense and store characteristics relating to components of downhole tool 20 as well as formation parameters at elevated temperatures and pressures.

Typical periods of operation for wireline tools are between 5 to 50 hours; for LWD tools between 1 day to 3 weeks; and for permanent monitoring tools from 1 year to 10 years or more. Thus, it is required that the sensing devices included in the downhole tool 20 should be capable of lengthening typical operational periods without servicing, increasing reliability and robustness of the downhole tool 20, and providing higher sensing sensitivity and selectivity over prior equipment.

The cable 22 may be a multiconductor logging cable, wireline, or other means of conveyance and/or communication that are known to persons skilled in the art. The service vehicle 10 includes a surface system 200. The surface system 200 may have appropriate electronics control and processing systems and telemetry capability for the downhole tool 20. The cable 22 typically is electrically coupled to the surface system 200.

Figure 2A:
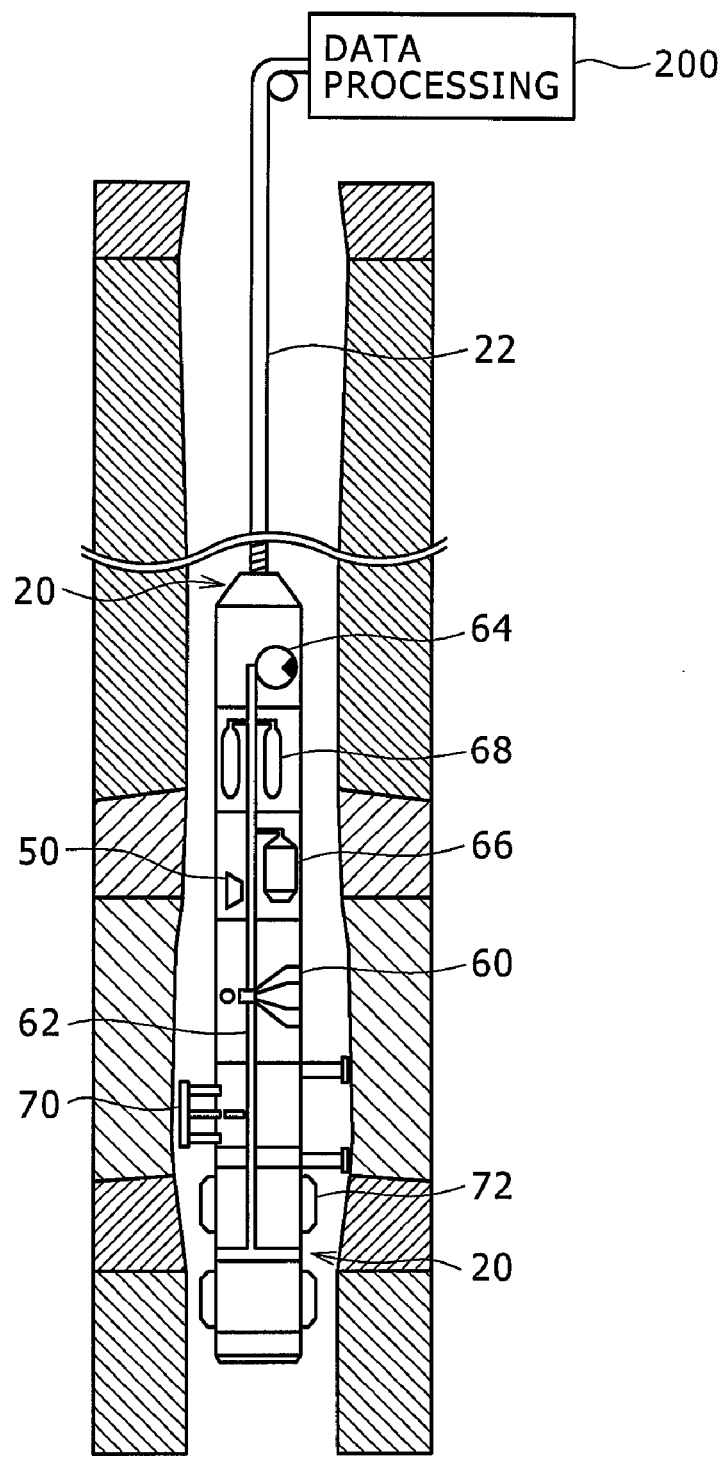
FIG. 2A shows one configuration for a downhole tool in accordance with the present disclosure.

FIG. 2(a) is an exemplary embodiment of a downhole tool sensing system for downhole analysis and sampling of formation fluids utilizing, for example, a chemical sensor module 50 according to the present disclosure. In FIG. 2(a), a borehole system for high temperature applications includes a borehole tool string 20, or other known means of deployment such as a drill collar, sonde, etc., for testing earth formations and analyzing the composition of fluids from a formation. The borehole tool 20 may be suspended in the borehole from the lower end of a multiconductor logging cable or wireline 22, or by other means of conveyance that are known to persons skilled in the art. The logging cable typically is electrically coupled to a surface system 200 having appropriate electronics, processing and telemetry systems for the borehole tool.

The borehole tool includes a variety of electronic components and modules, which are schematically represented in FIG. 2(a), for providing necessary and desirable functionality to the borehole tool. Examples of borehole tools are disclosed in commonly-owned U.S. Pat. Nos. 3,780,575, 3,859,851, and 4,860,581.

One or more fluid analysis modules 60 may be provided in the tool body. Fluids obtained from a formation and/or borehole flow through a flowline 62, via the fluid analysis module or modules 60 and chemical sensor module(s) 50, and then may be discharged through a port of a pumpout module 64. In this, chemical sensor modules could play a complementary role to fluid analysis modules which may not detect chemical species as sensitively as the chemical sensor modules. Alternatively, chemical sensor modules may replace fluid analysis modules as desirable or necessary for downsizing the downhole tools. Optionally, formation fluids in the flowline 62 may be directed to one or more fluid collecting chambers 66/68 for receiving and retaining the fluids obtained from the formation for transportation to the surface.

The fluid admitting assemblies, such as probe 70 and/or packer module 72, one or more fluid analysis modules 60 and/or chemical sensor modules 50, the flow path 62 and the collecting chambers 66/68, and other operational elements of the borehole tool, are controlled by electrical control systems. The system may include a control processor operatively connected with the borehole tool. Methods described herein may be embodied in a computer program that runs in the processor. In operation, the program is coupled to receive data, for example, from the fluid analysis module, via the cable, and to transmit control signals to operative elements of the borehole tool.

Figure 2B:
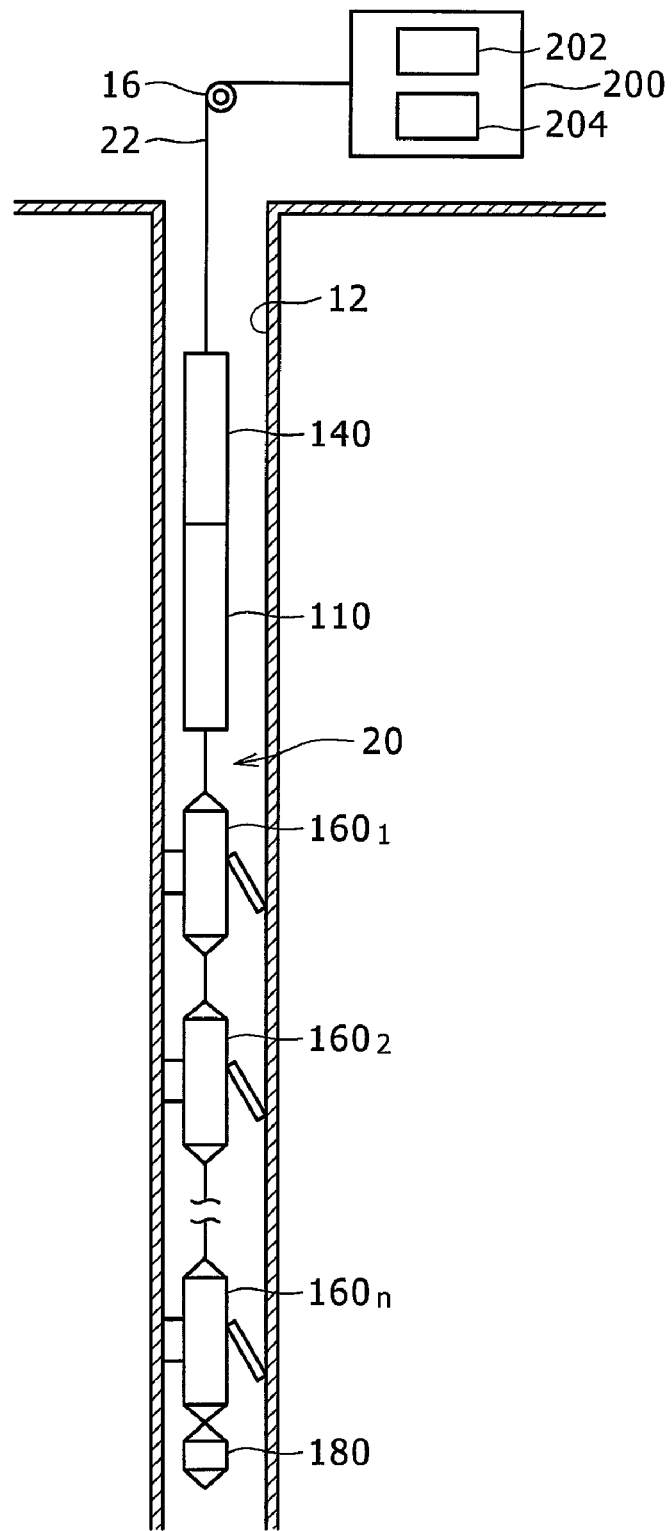
FIG. 2B shows yet another possible configuration for a downhole tool in accordance with the present disclosure.

FIG. 2(b) shows another possible embodiment of a surface control system 200 and downhole tool 20. In this embodiment, the surface system 200 includes a data communication unit 202 and a processing and control unit 204. The data communication unit 202 may include a control processor that outputs a control signal and is operatively connected with the downhole tool 20 via the cable or fiber 22 so that the control signal is delivered to the downhole tool 20. In this example, the downhole tool 20 includes a telemetry cartridge 140, an electronic cartridge 110 having, for example, an electrical tool bus, and an array of tool shuttles $160_1$, $160_2$, ..., $160_n$, and an array terminator 180 provided in this order from top to down in the borehole 12. The telemetry cartridge 140 communicates with the surface system 200. This structure is disclosed in commonly-owned U.S. Pat. No. 6,630,890, the contents of which are incorporated herein by reference in their entirety.

The downhole tool 20 of FIG. 2(b) may include a downhole sensing and data acquisition system placed in the electronic cartridge 110 and the array of tool shuttles $160_1$, $160_2$, ..., $160_n$.

Methods described herein may be embodied in a computer program that runs in the processor 204. The computer program may be stored on a computer usable storage medium associated with the processor, or may be stored on an external computer usable storage medium and electronically coupled to the processor for use as needed. The storage medium may be any one or more of presently known storage media, such as a magnetic disk fitting into a disk drive, or an optically readable CD-ROM, or a readable device of any other kind, including a remote storage device coupled over a switched telecommunication link, or future storage media suitable for the purposes and objectives described herein. In operation, the program is coupled to operative elements of the downhole tool 20 via the cable 22 in order to receive data and to transmit control signals.

Figures 3A, 3B:
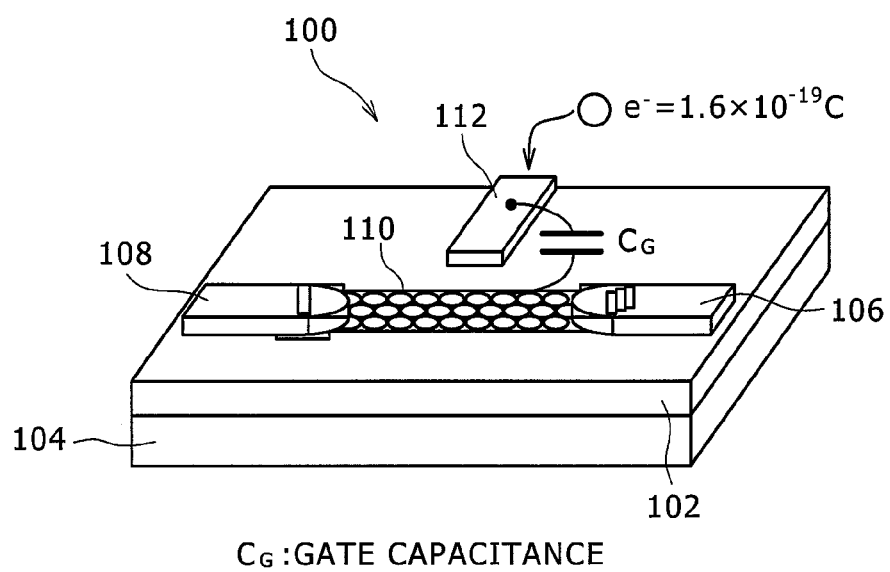
FIG. 3(a) is a schematic representation of the structure of a side-gate CNT FET.
FIG. 3(b) is a table showing a comparison of gate capacitance and voltage for a Si FET and a CNT FET.

FIG. 3(a) shows one embodiment of a CNT FET 100. The CNT FET 100 has a $SiO_2$ layer 102 on a substrate of Si semiconductor 104. A source electrode 106 and a drain electrode 108 are provided on the $SiO_2$ layer 102. The device of FIG. 3(a) is a field effect transistor (FET) with carbon nanotube (CNT) provided between the source electrode 106 and the drain electrode 108 to form a channel 110. A capacitance between gate electrode 112 and the channel 110 (hereinafter referred to as "gate capacitance" or "$C_G$") is estimated to be $10^{-17}$ to $10^{-18}$ F. The estimated capacitance is much lower than that of a Si FET (around $10^{-15}$ F). Accordingly, even if the surface charge of the gate electrode changes slightly due to an external stimulus, for example, contact with a particular chemical species, the gate voltage changes significantly.

FIG. 3(b) is a table showing the calculated sensitivities of a Si FET and a CNT FET. When an electron enters into the channel between a source electrode and a drain electrode, a CNT FET can have a much higher gate voltage ($V_G$) than a Si FET because of the difference in their gate capacitances ($C_G$).

The CNT FET illustrated in FIG. 3(a) is a side-gate FET in which the gate electrode 112 is disposed close to the channel 110. Such a side-gate CNT FET has a short channel, which is advantageous for circuit integration.

Figure 4:
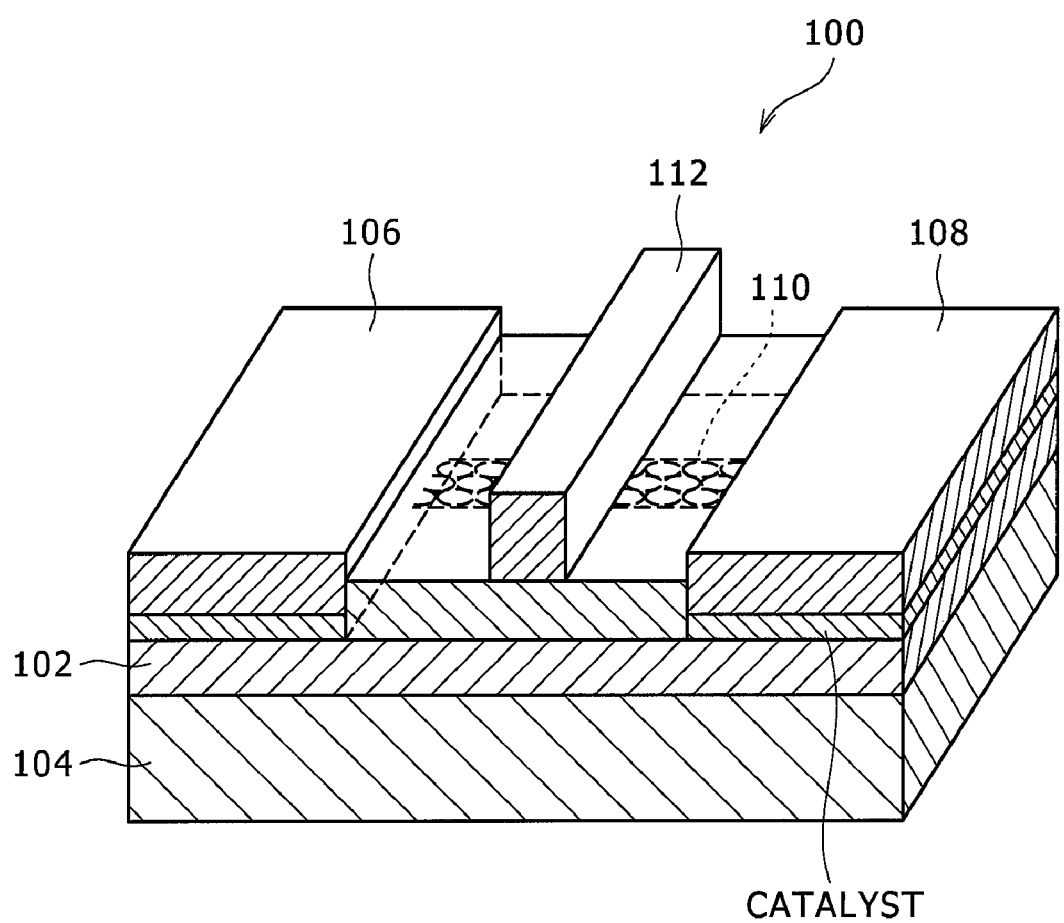
FIG. 4 shows a schematic illustration of a top-gate CNT FET.

FIG. 4 is a schematic illustration of a perspective view of a top-gate type CNT FET 100. Unlike the side-gate CNT FET of FIG. 3(a), the top-gate CNT FET has a gate electrode 112 on top of a CNT channel 110. A top-gate CNT FET has a gate electrode that is electrically separated. Such electrical separation is useful in an integrated circuit because individual CNT FET elements thereof can be electrically controlled.

Figure 5:
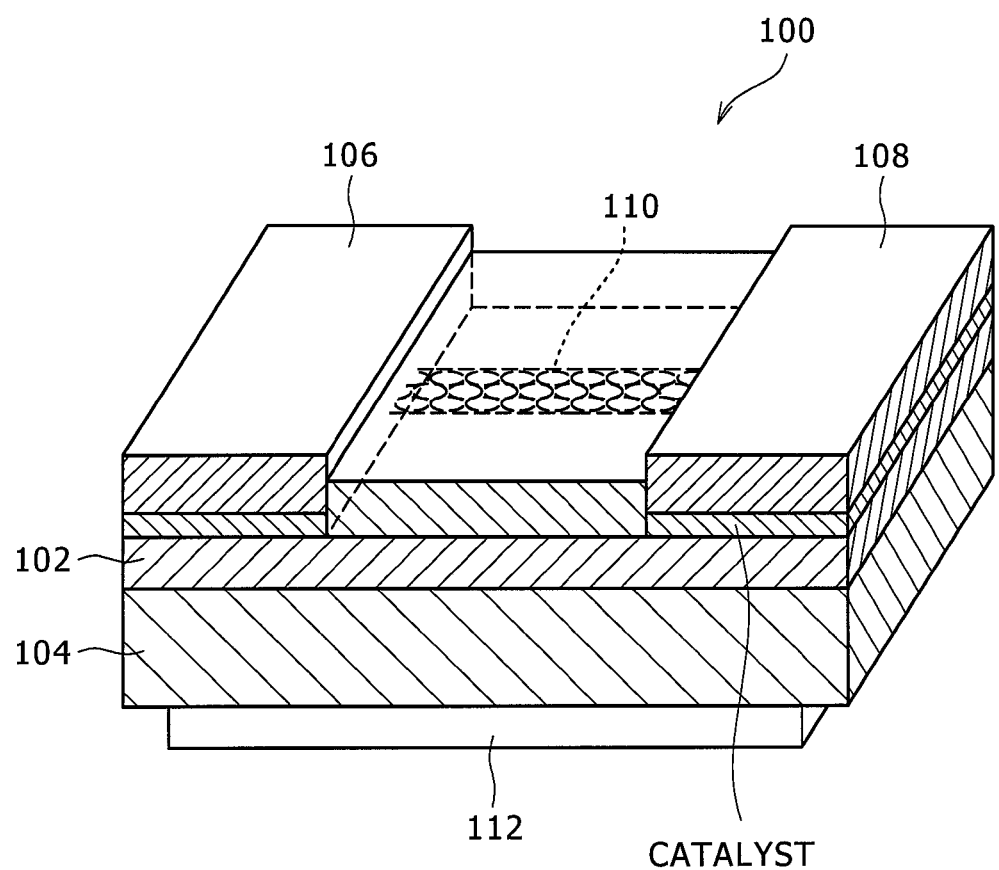
FIG. 5 shows a schematic illustration of a back-gate CNT FET.

FIG. 5 shows yet another embodiment of a CNT FET. The illustrated CNT FET 100 is a back-gate type CNT FET. In a back-gate CNT FET, a gate electrode 112 is provided at a back surface of a Si semiconductor substrate 104. The back-gate CNT FET has a structure that is different from the side-gate CNT FET of FIG. 3(a). The back-gate CNT FET has a short CNT channel 110 so that it is easy to attach a chemical probe to the back gate. The CNT channel 110 may be covered with a passivation layer of $Si_3N_4$. In FIG. 5, a catalyst layer 114 is provided on the $SiO_2$ layer 102 for growth of the CNT, as described in more detail below.

Figure 6:
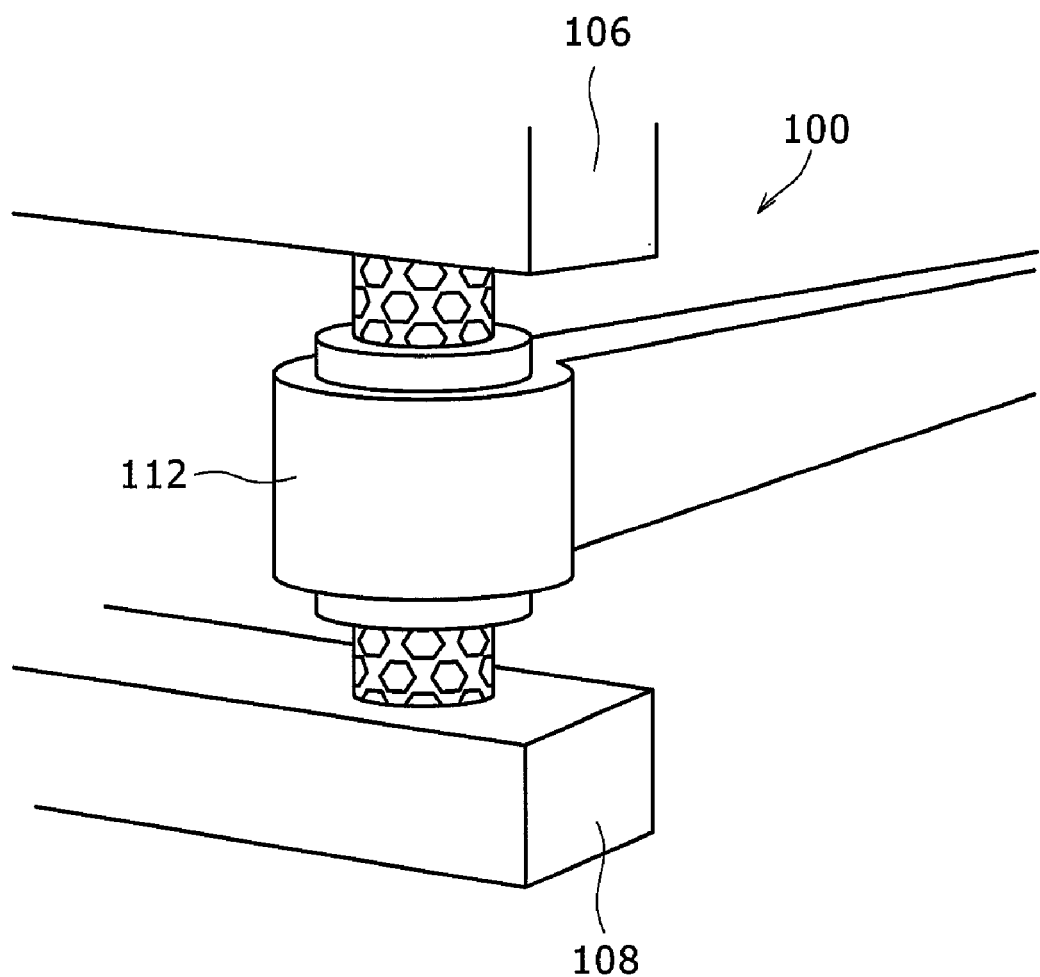
FIG. 6 shows a schematic illustration of a co-axial-gate CNT FET.

FIG. 6 shows another type of gate structure for a CNT FET. In FIG. 6 a co-axial gate electrode 112 is provided between the source electrode 106 and the drain electrode 108. The co-axial gate electrode of the FIG. 6 CNT FET covers the CNT with high geometrical symmetry and yields better electrical performance results.

Figure 7A:
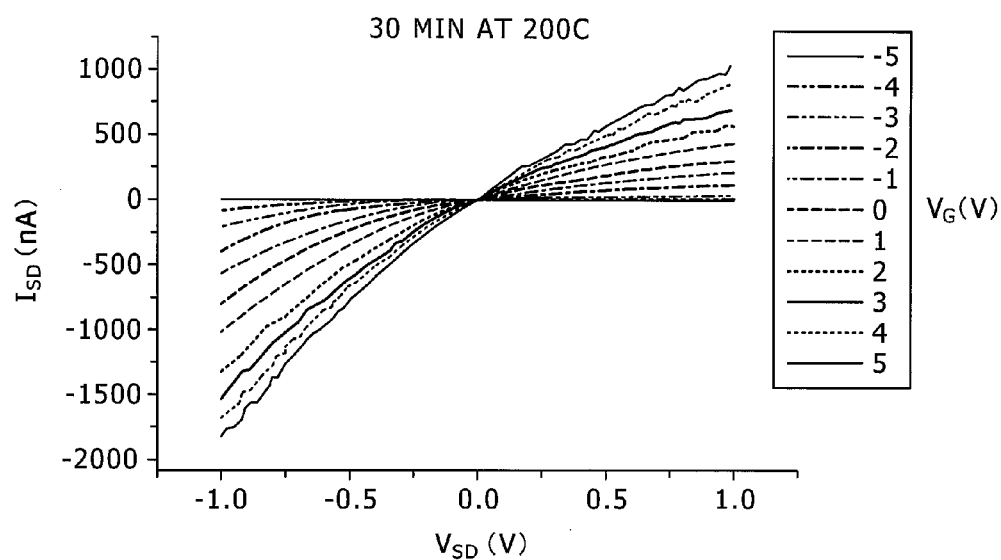
FIGS. 7(a) and 7(b) depict current-voltage characteristics of a back-gate CNT FET at high temperature.
Figure 7B:
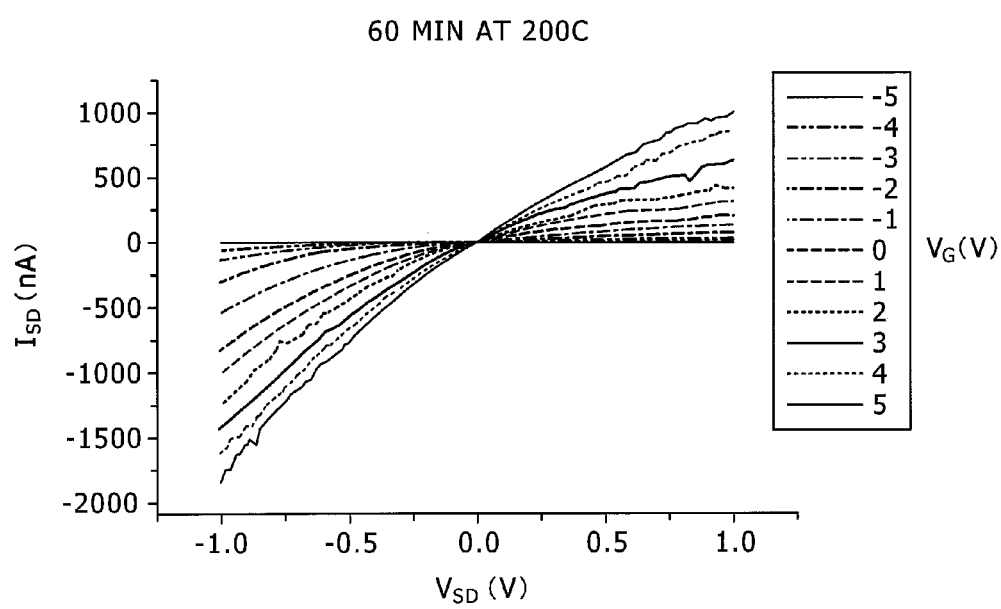

FIGS. 7(a) and 7(b) show current-voltage characteristics of a back-gate CNT FET at about 200 degrees Celsius and atmospheric pressure. As shown in FIGS. 7(a) and 7(b), as gate voltage ($V_G$) changes from −5V to +5V, source-drain current ($I_{SD}$) versus source-drain voltage ($V_{SD}$) changes accordingly. This indicates that a back-gated CNT FET can maintain semiconducting characteristics at 200 degrees Celsius for about one hour. Therefore, if a CNT FET is suitably packaged using existing packaging technology to protect from high pressure conditions, the CNT FET may be used in high pressure downhole environments.

Figure 8:
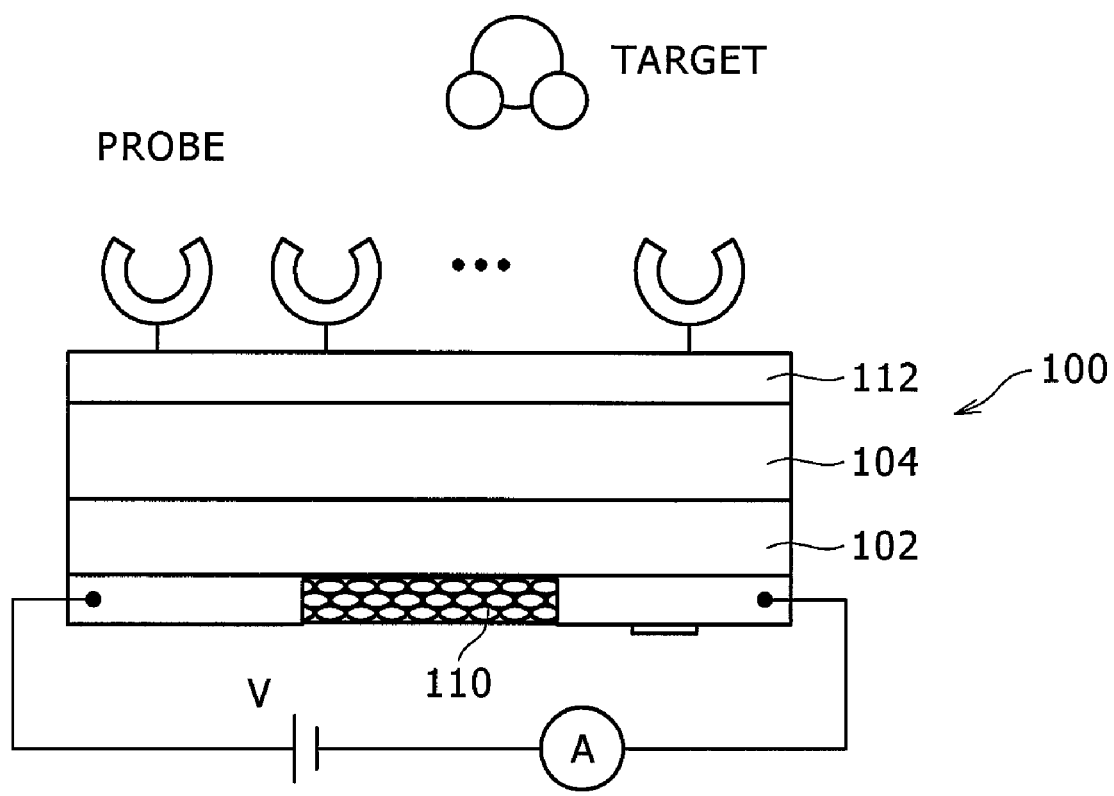
FIG. 8 is a schematic view of a back-gate CNT FET configured or designed as a chemical sensor according to the present disclosure.

The present inventors recognized that CNT FETs of the type described herein are particularly useful as chemical sensors. If a particular chemical species contacts with a gate electrode of a CNT FET, the gate electrode causes a gate capacitance to change, which results in significant change in the gate voltage of the CNT FET. FIG. 8 is a schematic depiction of a back-gated CNT FET that is configured or designed as a chemical sensor. In the CNT FET 100 of FIG. 8, the back-gate electrode 112 is physically or chemically modified so as to have a chemical probe attached thereto. The chemically-modified gate electrode has higher chemical selectivity. Alternatively, a chemical probe may be physically or chemically attached to the CNT FET. In this, any chemical probe that is suitable for the intended purpose may be used. For example, commonly-owned International Patent Publication Number WO2005/066618 discloses possible chemical probes that may be used in accordance with the principles described herein to measure vapors or gases such as $CO_2$, $H_2S$, Hg, $CH_4$, $C_2H_6$, $H_2$, among others, ions such as H+, Na+, Cl−, carbonate, sulphate, $Ba_2+$, $Ca_2+$, $Sr_2+$, or heavy hydrocarbon components such as asphaltenes.

If a CNT FET is configured or designed as a chemical sensor, the sensor would provide a very fast response to sensing chemical species. This is because a semiconducting CNT enables an electron and/or hole to move in the CNT without scattering due to the effect of ballistic conduction.

The present inventors further recognized that CNT may be used in various optical devices. A combination of a CNT FET with photo-materials provides a high sensitivity photo-detector in which the CNT FET is capable of high sensitivity in detecting photo-carriers generated in the photo-materials. A CNT that is semiconducting has an energy band gap that is dependent on the diameter. With control of the diameter, the semiconducting CNT can provide a suitable light receiving element, i.e., a photo detector, that is especially useful for downhole optical communications, fluorescence analysis and any other type of spectroscopy use. For example, commonly-owned and co-pending U.S. patent application Ser. No. 12/239,822 discloses some possible downhole tools having optical devices such as photo detectors that may be implemented according to the principles of the present disclosure.

FIG. 9 depicts schematically a light receiving element or photo detector 300. The light receiving element or photo detector 300 of FIG. 9 is similar to a back-gated or side-gated CNT FET except that there is no gate electrode. When a light beam, such as a laser beam, is incident to a CNT channel 110, a photoelectric current is generated between the drain electrode 108 and the source electrode 106 in accordance with a voltage there between. Such a composite structure having CNT may be applied to all photo-materials or multi-layered structures, which have photo-carriers generated inside, resulting in photo-detectors having high sensitivity in a wide range of wavelengths.

Figure 10:
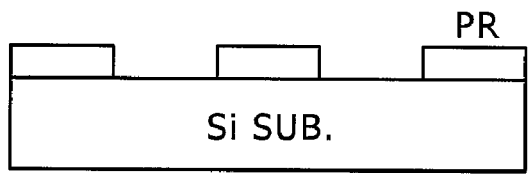
FIG. 10 illustrates one possible process for manufacturing a CNT FET according to the present disclosure.
Figure 10:
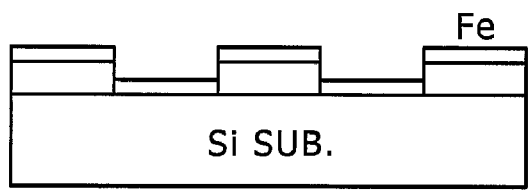
Figure 10:
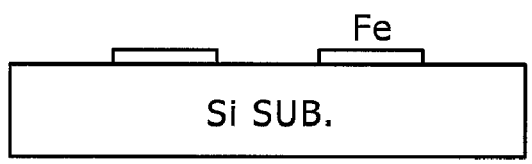
Figure 10:
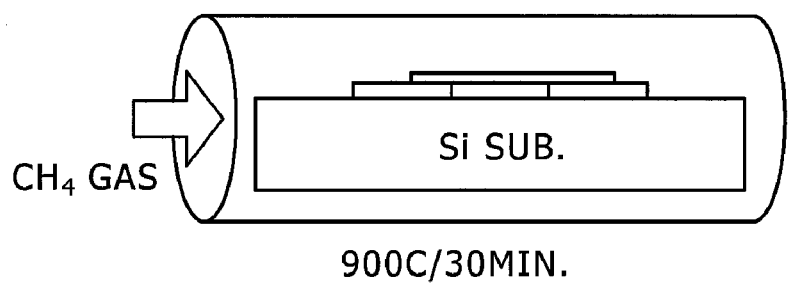

FIG. 10 illustrates one possible process for producing CNT FETs according to the principles of the present disclosure. In Step 1, a photoresist (PR) coating material is applied to a Si semiconducting substrate 104. If necessary, the coating material is then heated to remove a solvent thereof, and exposed to an ultraviolet, X or gamma ray or electron beam via a photo-mask. Next, when the coating material is developed, the substrate has a PR pattern layer formed thereon (FIG. 10 Step 1). The pattern layer illustrated in FIG. 10 has two separated recesses. After a catalyst with nanosized Fe particles is deposited on the substrate, the two recesses are filled with the catalyst (FIG. 10 Step 2). The catalyst is not limited to Fe; it may contain nanosized Ni, Co and/or any other transition metal particles.

In Step 3, the PR pattern layer is lifted off and only the filled catalyst portion remains. Next, in Step 4, the substrate with the catalyst portions is deposited in a reactor chamber, and a precursor gas of methane ($CH_4$) is flowed there through while the substrate is heated to around 900 degrees Celsius for about two hours. In this, the catalyst portions are exposed to the precursor gas, which reacts and/or decomposes with the catalyst portions to produce CNTs there between (FIG. 10 Step 4). The precursor gas is not limited to $CH_4$ gas; for example, $C_2H_2$ gas also may be used as a precursor gas.

Figure 11A:
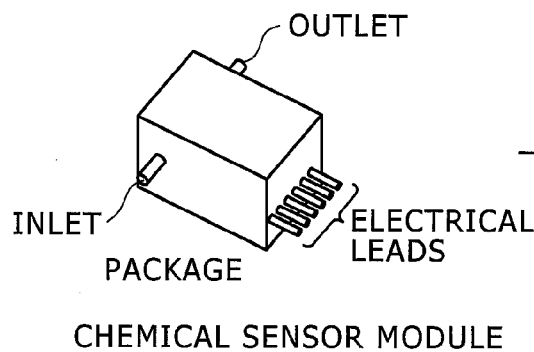
FIG. 11(a) depicts one possible chemical sensor module according to the present disclosure.
Figure 11B:
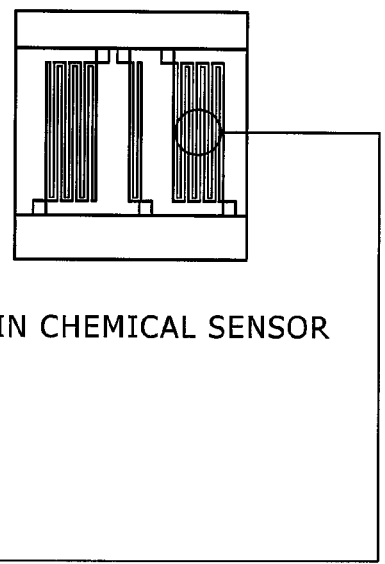
FIG. 11(b) depicts a microfluidics chip (MFC) in a chemical sensor module according to the present disclosure.
Figure 11C:
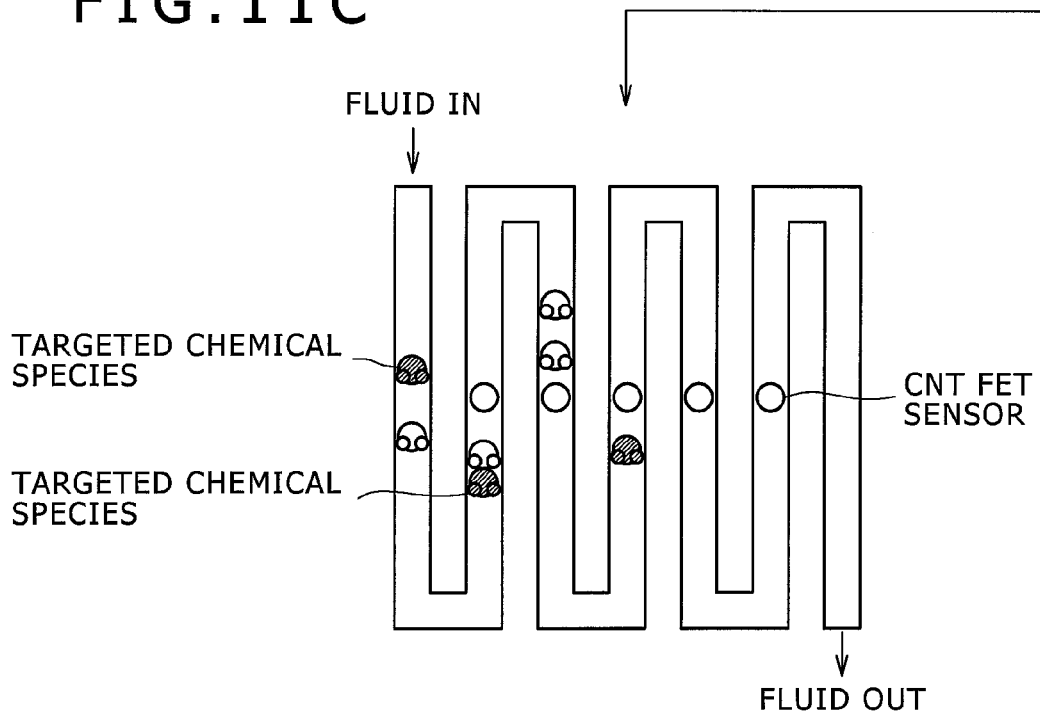
FIG. 11(c) is a schematic depiction of a fluid flow channel on an MFC according to the present disclosure.

The aforementioned CNT FET technology may be applied to a chemical sensor, as illustrated in FIGS. 11(a)-11(c). The chemical sensor module of FIG. 11 has a micro fluidics chip or lab-on-chip (MFC) packaging. An inlet and outlet are connected to the MFC (note FIG. 11(a)), to project from the package, so that formation fluid samples can be flowed through the MFC for fluids analysis. A MFC is a device having a micro channel on a glass substrate that is formed by a fine process technology. CNT FETs are placed in series with the micro channel of the MFC (note FIG. 11(c)). Each CNT FET may have a different chemical probe to detect different chemical species. When formation fluid samples are passed through the micro channel, the CNT FETs can selectively detect various targeted chemical species in the samples. The CNT FETs are electrically connected to electrical leads (note again FIG. 11(a)), which project from the package and send the electrical signals to other system electronics for processing and analysis.

The methods and electronics disclosed herein may be embodied in one or more fluid analysis modules of Schlumberger's formation tester tool, the Modular Formation Dynamics Tester (MDT). The modules may include sensors for detecting local environmental conditions such as pressure, temperature, fluid flow, and vibration. Surface data processing electronics may be coupled to a logging facility (not shown) that may gather, record, process, and analyze information telemetered thereto.

The principles described above are applicable not only to MEMS/microfluidics devices but also to macroscale sensor devices or systems. FIG. 12(a) depicts schematically another embodiment of a CNT FET sensing system having a gas detection unit 400 associated with a flow line 402. The flow line 402 is configured or designed for fluids, such as liquids having chemicals, for example, gas molecules, dissolved therein, to flow through. The flow line 402 has a gas detection chamber 404 connected thereto or embedded therein. The gas detection chamber 404 is in fluid communication with the flow line 402 via a selectively permeable membrane 406 that is selected for a targeted molecule of interest "A". A CNT FET sensor 408 is located opposite the membrane 406. The CNT FET sensor 408 is configured or designed with a probe layer that selectively captures the molecules of interest "A". Chemicals dissolved in a liquid in the flow line 402 are selectively separated such that gas molecules "A" enter into the gas detection chamber 404, via the selectively permeable membrane 406. The gas molecules "A" then move through the chamber 404 to contact with the CNT FET sensor 408. The CNT FET sensor 408 captures the gas molecules "A" with the probe for detection of gas "A".

It is contemplated that a plurality of gas detection units or chambers may be located on a single flow line. The plurality of gas detection units or chambers may be used to sense a single gas or a plurality of targeted gas molecules. Further, in order to sense a plurality of gas molecules, a detection unit or chamber may include additional CNT FET sensors with different probe layers. It is further envisioned that a gas detection unit may further comprise a heater so that gas molecules may be separated from the probe of the gas detection unit after detection. As a result, the gas detection unit may be used repeatedly.

Figure 12B:
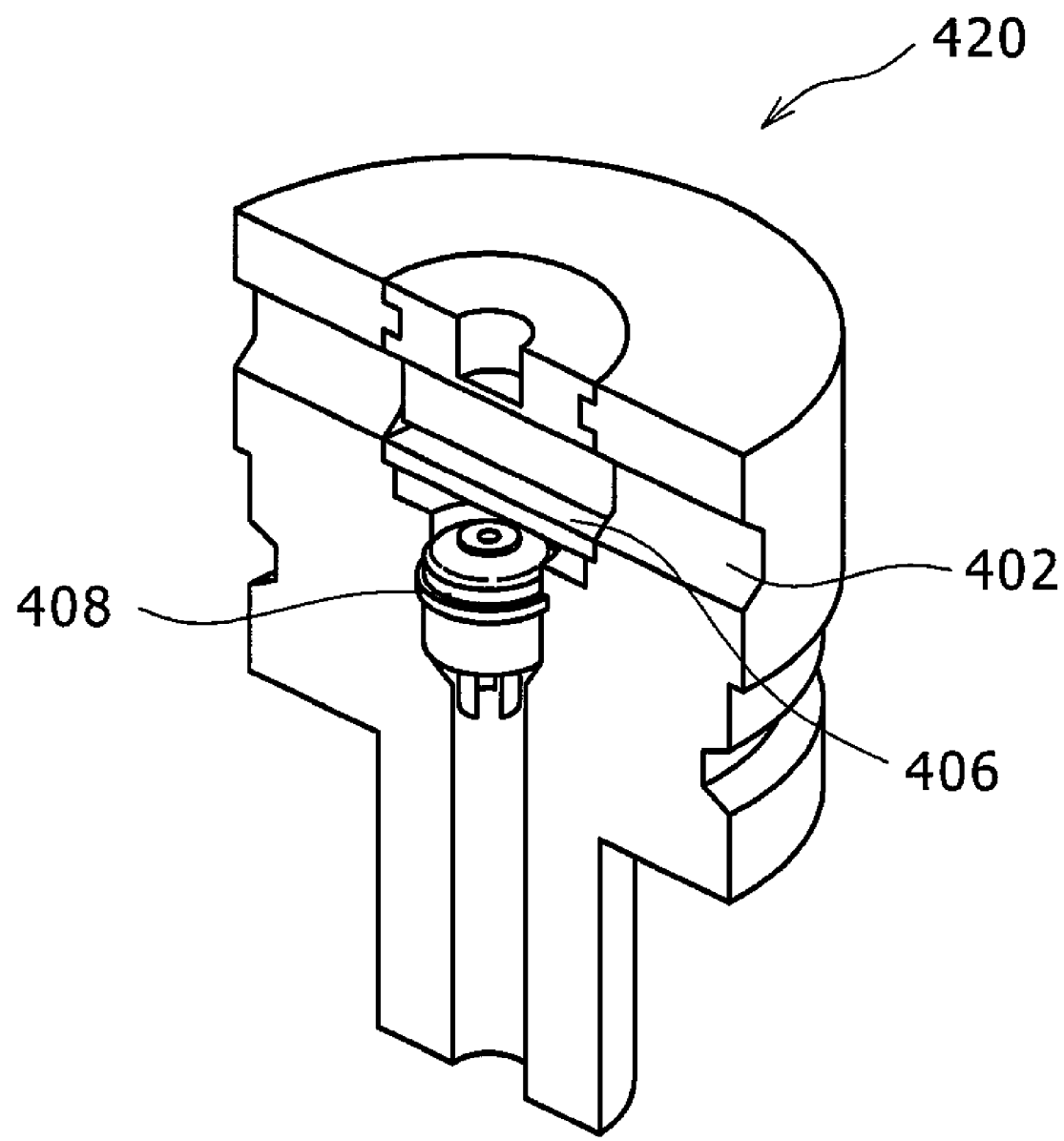

FIG. 12(b) illustrates one possible embodiment of a device based on the principles described above in connection with FIG. 12(a). In FIG. 12(b), a gas-separation membrane 406 is contained inside a sensor bulk head 420 having one or more CNT FET sensing units 408 therein. After separation of gas molecules by the membrane 406 the sensor 408 detects the gas molecules and generates corresponding signals that are outputted from the sensor bulk head 420.

The sensing systems disclosed herein may be utilized in wireline logging operations in a well using a sonde. Alternatively, coiled tubing may be employed for purposes of deploying the sonde in a wellbore. The sensing systems herein may be utilized for monitoring flow and for other applications relating to production, and production logging tools may be configured according to the sensing systems disclosed herein. Various chemical properties and chemicals may be measured with the aforementioned CNT FET chemical sensors. In this, the present disclosure also contemplates wireline or slickline tools for the sensing purposes described herein. Additional monitoring applications include fluid injection, formation fracturing, seismic mapping by downhole tools, among others that are known to one of ordinary skill in the art.

FIG. 13 illustrates one possible method 500 for tool operation in which a tool is deployed in a high temperature environment (Step 510), for example, about 115 degrees Celsius or above such as around 200 degrees Celsius, to acquire data relating to environmental parameters of the surrounding fluids and/or formations as well as density, viscosity, porosity and/or resistivity (Step 520). Furthermore, the tool may be used to acquire data relating to acceleration, pressure, rotation, vibration and/or temperature, or any other downhole tool performance parameter that is desirable or necessary for maintenance or operational history of the tool. Such data are then recorded and/or transmitted to remote receivers for processing and analysis (Step 530).

The preceding description has been presented only to illustrate and describe the invention and some examples of its implementation. It is not intended to be exhaustive or to limit the invention to any precise form disclosed. Many modifications and variations are possible in light of the above teaching.

The preferred aspects were chosen and described in order to best explain the principles of the invention and its practical application. The preceding description is intended to enable others skilled in the art to best utilize the invention in various embodiments and aspects and with various modifications as are suited to the particular use contemplated. It is intended that the scope of the invention be defined by the following claims.

What is claimed is:

1. A subterranean tool downhole in a well traversing a formation, comprising:
    a sensing device configured or designed for downhole use to sense a local condition in the well, wherein
        the sensing device comprises one or more transistor, wherein
            the one or more transistor comprises at least one carbon nanotube field effect transistor (CNT FET) configured or designed for operation downhole, within a borehole; and
        the sensing device further comprises at least one optical device, wherein
            the optical device comprises the at least one CNT FET configured or designed to function as a photo-sensitive detector downhole, within a borehole.

2. A subterranean tool according to claim 1, wherein the at least one CNT FET is configured or designed for sensing physical and/or chemical characteristics downhole, within a borehole.

3. A subterranean tool according to claim 1, wherein the at least one CNT FET comprises a side-gate FET.

4. A subterranean tool according to claim 1, wherein the at least one CNT FET comprises a top-gate FET.

5. A subterranean tool according to claim 1, wherein the at least one CNT FET comprises a back-gate FET.

6. A subterranean tool according to claim 1, wherein the at least one CNT FET comprises a co-axial gate FET.

7. A subterranean tool according to claim 1, wherein the at least one CNT FET is configured or designed for use at downhole temperatures in excess of about 115 degrees Celsius.

8. A subterranean tool according to claim 7, wherein the at least one CNT FET is configured or designed for use at downhole temperatures of about 200 degrees Celsius.

9. A subterranean tool according to claim 1, wherein the at least one CNT FET is modified to function as a chemical probe.

10. A subterranean tool according to claim 1, further comprising:
    a chemical probe, the chemical probe being fixed to the at least one CNT FET.

11. A subterranean tool according to claim 1, wherein the subterranean tool comprises one or more optical communications module including the at least one optical device.

12. A subterranean tool according to claim 1, wherein the subterranean tool comprises one or more downhole fluid analysis module including the at least one optical device.

13. A subterranean tool according to claim 1, wherein the sensing device comprises a chemical sensor.

14. A subterranean tool according to claim 13, wherein the chemical sensor comprises a gas detector.

15. A downhole chemical sensing system, comprising:
    a surface data acquisition unit comprising a surface telemetry unit;
    a downhole telemetry cartridge;
    a communications interface between the surface data acquisition unit and the downhole telemetry cartridge;
    a downhole tool; and
    a downhole electrical tool bus operatively connected between the downhole telemetry cartridge and the downhole tool, wherein
    the downhole tool comprises:
        a chemical sensing device configured or designed for downhole use to sense a local condition in a well, wherein
            the chemical sensing device comprises one or more carbon nanotube field effect transistor (CNT FET) configured or designed for operation downhole, within a borehole, to sense chemical characteristics.

16. A downhole chemical sensing system according to claim 15, wherein
    at least one CNT FET is modified to function as a chemical probe.

17. A downhole chemical sensing system according to claim 15, wherein
    the chemical sensing device comprises a chemical probe, the chemical probe being fixed to at least one CNT FET.

18. A downhole chemical sensing system according to claim 15, wherein
    the chemical sensing device comprises a gas detector.

19. A fluid analysis system configured to operate downhole at elevated temperatures in excess of about 115 degrees Celsius in a well traversing a formation, comprising:
    at least one optical sensor to measure signals of interest and determine properties of formation fluids downhole, within a borehole, wherein
    the at least one optical sensor comprises one or more carbon nanotube field effect transistor (CNT FET) configured or designed for operation downhole, within a borehole, as a photo-sensitive detector, the CNT FET being configured or designed for operation downhole, within a borehole, at temperatures in excess of about 115 degrees Celsius.

* * * * *